(12) United States Patent
Rindt

(10) Patent No.: US 6,905,872 B1
(45) Date of Patent: Jun. 14, 2005

(54) ON-LINE RESPIROMETER AND METHOD OF USING THE SAME

(76) Inventor: John R. Rindt, P.O. Box 5192, Grand Forks, ND (US) 58206-5192

(*) Notice: Subject to any disclaimer, the term of this patent is extended or adjusted under 35 U.S.C. 154(b) by 178 days.

(21) Appl. No.: 10/172,114

(22) Filed: Jun. 14, 2002

(51) Int. Cl.$^7$ ................................................ C12M 3/00
(52) U.S. Cl. ............................. 435/287.5; 435/286.6; 435/287.1
(58) Field of Search .......................... 435/287.1, 286.6, 435/287.5

(56) References Cited

U.S. PATENT DOCUMENTS

| | | | |
|---|---|---|---|
| 3,731,522 A | 5/1973 | Mikesell | ................... 73/19 |
| 4,783,172 A | 11/1988 | Garg | ................... 366/142 |
| 4,947,339 A | 8/1990 | Czekajewski et al. | ...... 364/497 |
| 5,125,262 A | 6/1992 | Garg | ................... 73/19.12 |
| 6,063,617 A | 5/2000 | Young et al. | ............ 435/287.5 |

*Primary Examiner*—Leon B. Lankford, Jr.
*Assistant Examiner*—Ruth A. Davis
(74) *Attorney, Agent, or Firm*—Thomte, Mazour & Niebergall; Shane M. Niebergall

(57) ABSTRACT

An on-line respirometer and method for using the same is disclosed for determining the oxygen uptake of respiring samples. An overflow drain in the side portion of an enclosed reaction vessel is located to define an operational volume of slurry sample and headspace gases. The slurry sample is agitated using a mixer and/or a pump which recirculates the headspace gases through the slurry. Oxygen probes inserted into the headspace and the slurry sample determine the level of dissolved oxygen within the slurry sample and the headspace. The fixed ratio of available oxygen to oxygen demand is sufficient to measure the oxygen uptake directly, without the need for oxygen supplementation, for simple, fast and accurate analysis.

9 Claims, 2 Drawing Sheets

ON-LINE RESPIROMETER AND METHOD OF USING THE SAME

BACKGROUND OF THE INVENTION

1. Field of the Invention

The present invention relates generally to respirometers and more particularly to an on-line respirometer for quickly and accurately evaluating the biological activity levels for suspended biological matter.

2. Description of the Prior Art

Methods of sewage treatment typically involve the retention of the treated sewage in a processing tank until the biological population (bacteria) within the sewage has consumed a sufficient amount of the available nutrients so that the biological population will not grow to an unacceptable level when the sewage is released. Treated sewage is typically released into fresh water disposal areas. If the sewage is introduced to the disposal area containing an excessive biological population, the biological population will continue to grow rapidly and consume the oxygen in the body of water at a rate higher than that in which oxygen is absorbed by the body of water. Eventually, the dissolved oxygen within the body of water will be depleted, killing any animals living within the body of water. Therefore, it is crucial that the rate of oxygen consumption in the sewage be known prior to its disposal.

Respirometers have been commonly used to monitor the oxygen consumption rate of treated sewage prior to its disposal. Many different respirometer designs and methods of using the same have been incorporated in the treatment of sewage. Most prior art respirometers usually comprise a reaction vessel, a method of inserting a sewage slurry sample into the vessel, and a means for monitoring the pressure change in the reaction vessel.

One such type of respirometer requires the user to insert the slurry sample (containing a measured amount of a biological population and sewage). The user then introduces a measured amount of oxygen to the reaction vessel and aerates the slurry sample. The pressure drop is then measured, and the entire process is repeated a number of times to create a long-term record of oxygen uptake. This type of respirometer suffers from a number of problems. First, this method of respirometry requires the sewage to be diluted with aerated water prior to measurements being taken. Second, the user is required to test sequential batch reactions and is unable to create a true record of continuous oxygen uptake from the sample.

In another type of on-line respirometry, the biological population is first mixed with oxygen-enriched air so that the dissolved oxygen concentration remains relatively constant throughout the test. When the sewage sample is added, the dissolved oxygen concentration will begin to decrease as the biological population consumes the oxygen within the slurry. However, the level of oxygen concentration will typically begin to increase as the rate of oxygen transferred into the sample exceeds the rate of oxygen uptake by the biological population. This process is repeated several times to generate a consumption curve. One problem with this method of respirometry is the large number of repetitive measurements required to obtain a meaningful indication of the rate of oxygen uptake. Another problem is that the results are dependent on the mass transfer characteristics, which are subject to considerable variability over time.

In another common method of respirometry, the oxygen uptake is measured in a continuous fluid flow system, which can either be mobile or fixed with respect to the biological population flow. The decreases in dissolved oxygen concentration are measured and recorded on a continuous basis. The biological oxygen demand is derived by correlating the oxygen uptake rate to a standard measure of biochemical oxygen demand. This method of respirometry is problematic in that the decrease in oxygen concentration across the reaction vessel must be relatively large in order to obtain an accurate measurement of the oxygen uptake. This lack of sensitivity may result in inaccurate test results.

In yet another method of respirometry, both the fluid and gas phases of the test medium are tested in continuous flow streams. The consumption of oxygen is determined by the volume of fresh air or oxygen flowing into the vessel and the dissolved oxygen level in either the headspace or the slurry sample. One of the problems with such a system is that the change in oxygen content of the air stream must be relatively large to provide an accurate calculation of oxygen consumption by the biological population. Again, this lack of sensitivity may skew the final test results.

Each of the aforementioned methods of respirometry require large changes in dissolved oxygen concentration or headspace oxygen content to produce measurements of oxygen uptake. However, U.S. Pat. No. 6,063,617 discloses a method of respirometry that does not require the measurement of such large changes in order to determine the rate of oxygen uptake for a given sample. That method involves the measurement of the amount of supplementary oxygen that must be injected into a reaction vessel to maintain a consistent dissolved oxygen concentration in the slurry sample. The oxygen is automatically injected into the vessel in response to the changes of oxygen that occur within the sample. However, this method of respirometry is also susceptible to a lack of sensitivity and high levels of complexity due to multiple, sequential instrument error and requires long periods of time to measure respiration changes.

Accordingly, what is needed is an on-line respirometer and method of using the same that simply and accurately measures the rate of oxygen uptake of a biological population in a slurry sample within a time frame which will allow its use to assist in the control of variables which can accompany biological needs change during events such as diurnal flow and composition variations.

SUMMARY OF THE INVENTION

The on-line respirometer of the present invention is characterized by an enclosed reaction vessel having an inlet and overflow drain to receive and expel respiring samples such as sewage slurry samples. Excess slurry sample is inserted into the vessel so that a portion of the slurry sample is expelled from the system via the overflow drain. This provides for a constant volume of slurry sample within the vessel for each procedure. The headspace of the vessel is then charged with a reactant gas, and the vessel is sealed. The constant ratio of headspace gas to slurry sample for each procedure provides a uniform ratio of available oxygen to oxygen demand. The ratio is selected to be great enough so that the biological population within the slurry sample is not adversely affected. However, the ratio is also determined to be small enough so that sensitive measurements of the change in dissolved oxygen within the system can be detected and recorded.

The slurry sample is agitated using a variable speed prop mixer. The slurry sample can also be agitated through the recirculation of the headspace gases. A pump is used to draw the headspace gases from the top portion of the vessel and reintroduce the gases directly into the slurry sample adjacent the bottom portion of the vessel. While the sample is being agitated, a dissolved oxygen probe disposed within the slurry sample continuously measures the dissolved oxygen levels within the sample. Simultaneously, a second dissolved oxygen probe, disposed within the headspace, measures the oxygen content of the headspace gases. Information from the probes is displayed on dissolved oxygen meters.

The oxygen uptake readings taken by the respirometer are done without the necessity of a high volume of sample material or the measured insertion of pure oxygen into the system. The result is a simple respirometer that provides accurate, on-line measurements of oxygen uptake in a relatively short period of time.

Accordingly, it is one of the primary objectives of this invention to provide an online respirometer capable of quickly and accurately determining the oxygen uptake of a respiring sample.

It is another object of this invention to provide an on-line respirometer that is capable of measuring the oxygen uptake of a respiring sample without injecting measured amounts of additional reactant gases throughout the process.

It is yet another object of this invention to provide an on-line respirometer that fixes the ratio of available oxygen to biological demand, within a desired range of accuracy, to allow for the direct measurement of oxygen uptake.

It is still another object of this invention to provide an on-line respirometer capable of determining activation levels for biological matter.

These and other objects will be apparent to those skilled in the art.

DESCRIPTION OF THE PREFERRED EMBODIMENT

Figure 1:
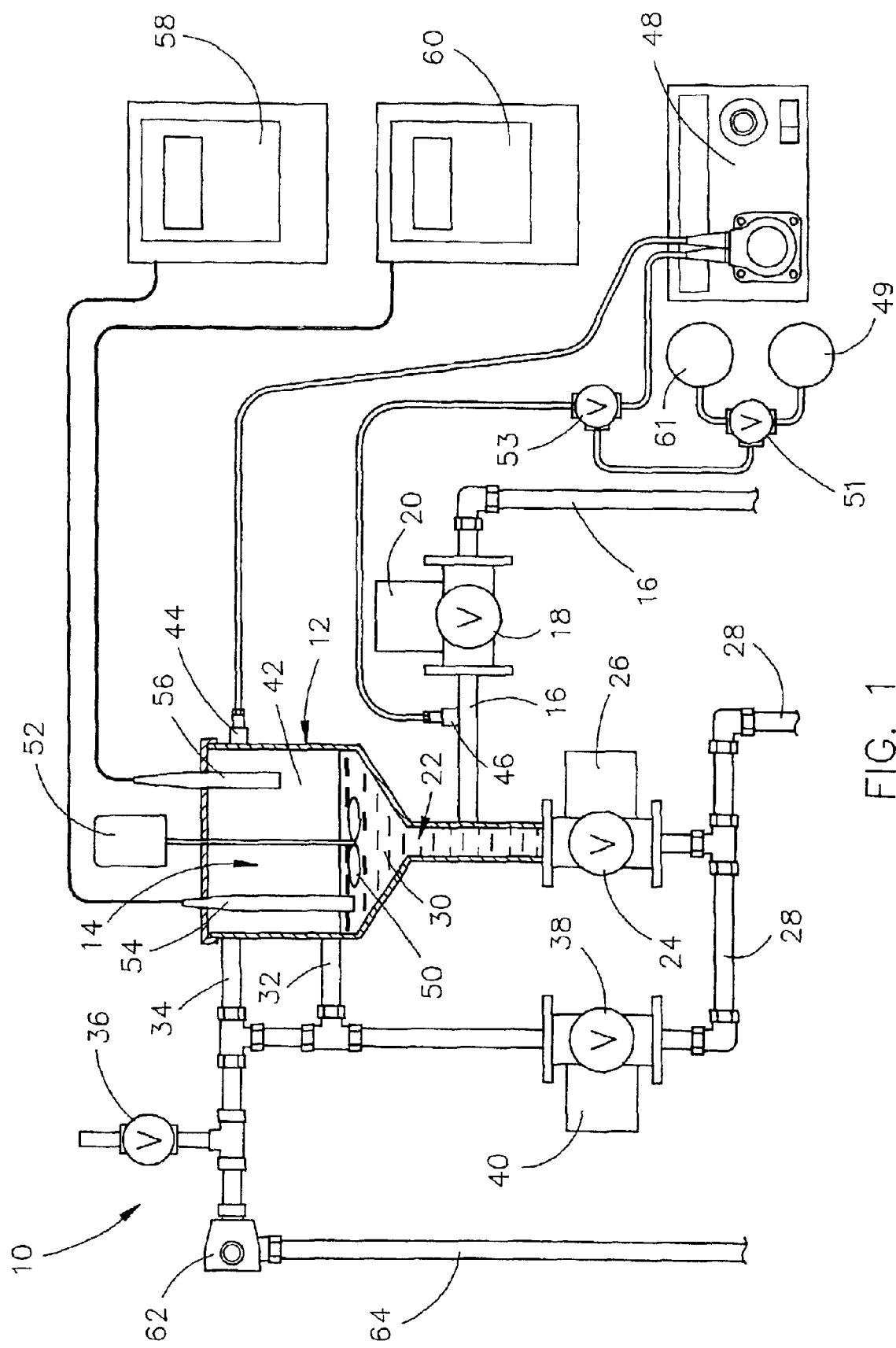
FIG. 1 is a schematic view of the on-line respirometer of this invention.

FIG. 1 depicts the on-line respirometer 10 of the present invention. The apparatus and method of using the same disclosed herein can be used to determine the oxygen uptake of nearly any type of respiring sample. However, for descriptive purposes only, the respirometer 10 will be described herein as it would be used in the process of treating sewage and similar wastewaters.

The respirometer 10 of the present invention is provided with an enclosed reaction vessel 12, having an inner chamber 14. A respiring sample, in this example a sewage slurry sample comprising a mixture of sewage and an aqueous culture of microorganisms (biological population), is delivered to the respirometer 10 by a sewage slurry line 16. In the present example, the sewage slurry line 16 would typically be fed from an analytical board pump in a wastewater treatment facility. Although delivery pressures will vary from facility to facility, the sample in the present example is delivered at 10 psi. The flow of the sewage slurry sample is controlled using the slurry valve 18, which is automatically or manually controlled using a slurry valve actuator 20. When the slurry valve 18 is opened, the slurry sample is delivered to the inlet 22 of the reaction vessel 12. The inlet 22 further serves as a master drain for the reaction vessel 12 when testing of the slurry sample is complete. The sample is released from the inlet 22 and is passed through a first drain valve 24 which is automatically or manually operated using a first drain valve actuator 26. The slurry sample may then pass through drain line 28 for disposal.

As the slurry sample is pumped into the inner chamber 14 of the reaction vessel 12, it produces a rising volume of slurry sample 30. Disposed within the side of the reaction vessel 12 is an overflow drain 32, which is in operative communication with the inner chamber 14. As the slurry sample 30 is pumped into the enclosed reaction vessel 12, the vacuum of the enclosed reaction vessel 12 prevents the complete discharge of the slurry sample 30 through the overflow drain 32. It is preferred that the volume of the slurry sample 30 rise above the overflow drain 32. When the volume has surpassed that point, a vacuum break 34, located near the top of the reaction vessel 12, is actuated using a vent 36. By releasing the vacuum pressure, the excess amount of slurry sample 30 is allowed to exit the reaction vessel 12 through the overflow drain 32. The excess slurry sample 30 then passes through a second drain valve 38, which is automatically or manually operated using a second drain valve actuator 40. The excess slurry sample 30 passes through the drain line 28 for disposal.

The level of the slurry sample 30 will be constant for each procedure through the use of the overflow drain 32. Due to the fact that the size of the inner chamber 14 remains constant, a constant volume of headspace 42 will be consistently produced above the slurry sample 30. Once the slurry sample 30 and the headspace 42 have reached their predetermined volumes, the vent 36 is closed and a gas outlet 44, positioned near the upper portion of the reaction vessel 12, is opened. Either the headspace 42, or slurry sample 30, is then purged of existing gases and charged with a gas containing a reactant gas such as oxygen. The gas that is used will vary from application to application and may be oxygen, air or other desired gas mixture. The gas is inserted into the respirometer 10 at a gas inlet 46. While FIG. 1 depicts the gas inlet 46 being connected with the sewage slurry line 16, it is contemplated that the gas inlet 46 could be connected directly to the reactant vessel 12. The gas is driven through the gas inlet 46 using a pump 48. Although many styles of pumps could be used in this application, the present example uses a peristaltic pump 48. When a particular reactant gas is to be used, the gas can be supplied using an external supply 49, which is coupled to the line leading away from the pump 48. The flow from the external supply is controlled using automated valves 51 and 53. The pump 48 is also coupled with the gas outlet 44. In this configuration, the gases within the headspace 42 can be circulated through the slurry sample 30 to agitate the same and provide an exchange of gases. The pump 48 is a variable speed pump to accommodate different reaction rates and activity levels.

The slurry sample 30 can also be agitated during the procedure using a mechanical mixer 50. Although it is contemplated that other forms of mechanical mixers may be used, such as a paddle mixer or a stirring magnet, the present example is provided with a variable speed prop mixer 50, which is powered by an electric motor 52. It is preferred that the mixer 50 have a speed range that is large enough to go from laminar to very turbulent flow mixture rates. This is desirable so that the mixing action can be conformed to the varied viscosities and solids loads expected in the processing of wastewaters such as sewage. Due to their separate nature, it is contemplated that the mechanical mixing of the slurry sample 30 and the aeration of the slurry sample 30 could be done separately or simultaneously.

A first oxygen probe 54 is disposed within the inner chamber 14 and is positioned so that it will be in operational contact with the slurry sample 30. A second gas probe 56 is disposed within the inner chamber 14 but remains only in operational contact with the headspace 42. These gas probes are connected to an external first dissolved oxygen meter 58 and a second dissolved oxygen meter 60, respectively. Accordingly, as the slurry sample is agitated during the process, direct continuous readings of the subject reactant gases (in this example dissolved oxygen within the slurry sample 30 and oxygen within the gases of the headspace 42) are conveniently provided. In the current configuration, the dissolved oxygen meters 58 and 60, as well as the mixer 52, pump 48, and all associated valves, are directly connected to a programmable controller and data requisition system to both control the function of the system and provide data collection, data reduction, and operational communication to the wastewater treatment plant.

The preferred use of the respirometer 10 involves the use of gases having a known content. Accordingly, it is desired to know the oxygen content of the ambient air if that is the gas to be used. By knowing the content of the gas and the reactant gas within, another known variable is provided. By knowing the consistent ratio of volumes between the headspace 42 and the slurry sample 30, a known ratio of available oxygen to oxygen demand of the biological population can easily be produced. It is preferred that the ratio of available oxygen to oxygen demand be large enough that the biological population is not adversely affected due to a lack of reactant gas during the data collection period. However, by providing a ratio of available oxygen demand that does not greatly exceed the needs of the biological population, sensitive and consistently accurate measurements of oxygen uptake by the biological population can be made. This allows the user to use a one-step data acquisition regime (direct measurement of dissolved oxygen), and use both the known volumes of the headspace 42 and the slurry sample 30 to determine the rate at which the oxygen is consumed, as well as the rate of transfer from the headspace 42 to the slurry sample 30.

Figure 2:
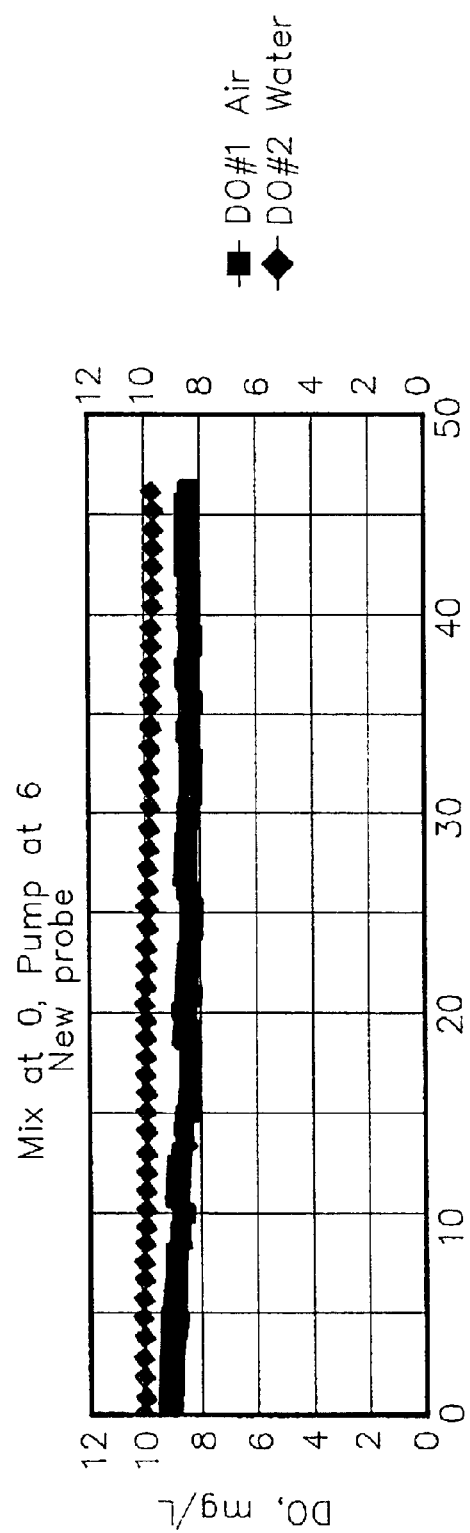
FIG. 2 is a graph of the results of a respirometry test of this invention utilizing a low liquid mixing rate and a high gas recycle rate.
Figure 3:
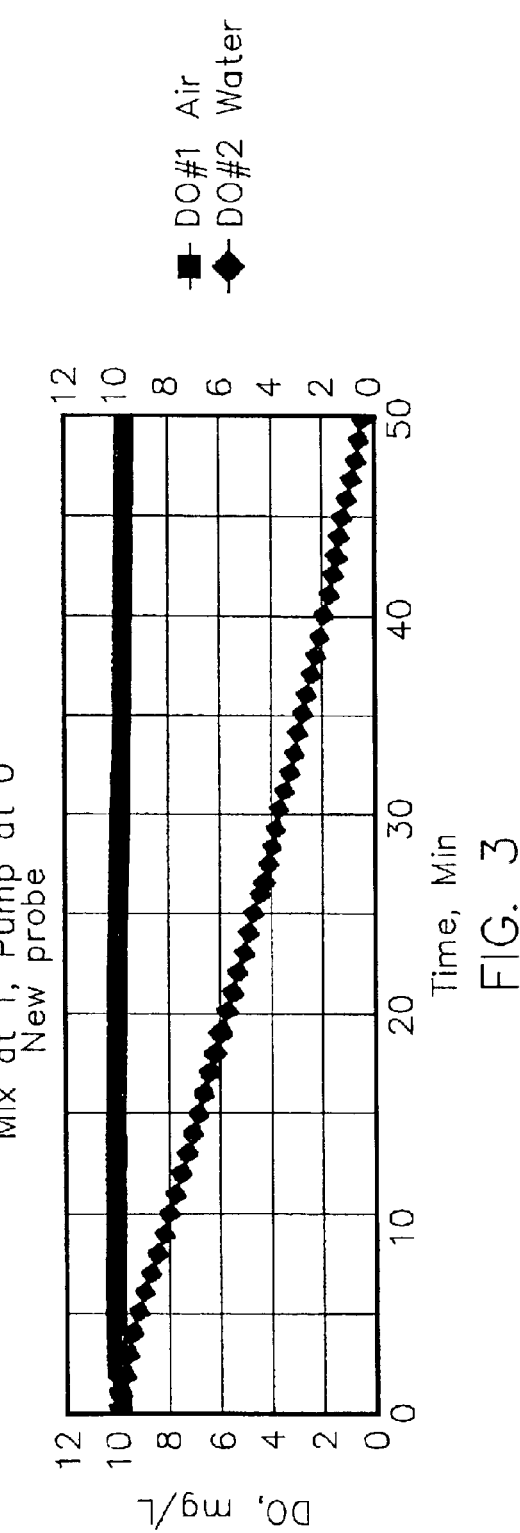
FIG. 3 is a graph of the results of a respirometry test of this invention utilizing a high liquid mixing rate and a no gas phase mixing.

By using the analytical practice of internal standards (quantitative aliquots of sample and reactive gas), a large portion of the errors experienced by the prior art, due to a lack of sensitivity, is eliminated. Moreover, the accuracy of the present system is increased by virtue of the fact that the oxygen uptake is being measured directly rather than through secondary measurements of an added reactant gas, as practiced by the prior art. In combination with the ability to add a known quantity of excess nutrient from an external nutrient source 61, the state of activation for an aliquot of biological slurry, as well as the portion of the biological population that is still viable can be easily determined on-line within an approximate range of 10 to 40 minutes. FIGS. 2 and 3 depict graphical results of example tests using the methods of the present invention.

Once the testing is complete, the slurry sample 30 is removed from the system through the inlet 22 and out the drain line 28 for disposal. The system can then be cleaned by the actuation of a potable water valve 62, which is coupled to a potable water line 64. The water enters the reaction vessel 12 through the vacuum break 34. Through the activation and deactivation of the various valving of the respirometer 10, each of the lines can be flushed with water so that future testing will not be contaminated by residue of the previous slurry sample 30.

In the drawings and in the specification, there have been set forth preferred embodiments of the invention; and although specified items are employed, these are used in a generic and descriptive sense only and not for purposes of limitation. Changes in the form and proportion of parts, as well as substitute of equivalents, are contemplated as circumstances may suggest or render expedient without departing from the spirit or scope of the invention as further defined in the following claims.

Thus it can be seen that the invention accomplishes at least all of its stated objectives.

I claim:

1. An on-line respirometer for conducting a test of the activation level of a biological population, comprising:

a slurry sample containing a biological population;

a single, predetermined volume of reactant gas;

a reaction vessel having an upper end, a lower end, and an inner chamber;

a slurry inlet operatively connected to said reaction vessel to selectively deliver said slurry sample to said inner chamber;

a gas inlet operatively connected to said reaction vessel to selectively introduce a gas, comprising said single predetermined volume of reactant gas, to said inner chamber;

an agitator disposed at least partially within said inner chamber for selectively mixing the slurry sample;

an overflow drain operatively connected to said reaction vessel intermediate the upper and lower ends thereof; said overflow drain being positioned to define an operational volume of headspace, an operational volume of said slurry sample and said single predetermined volume of reactant gas to provide accurately repeatable tests of the activation level of biological populations; and sensor means for determining the amount of reactant gas within said inner chamber.

2. The on-line respirometer of claim 1 wherein said single predetermined volume of reactant gas at least great enough to sustain the biological population within said slurry sample throughout the test.

3. The on-line respirometer of claim 1 wherein said single predetermined volume of reactant gas is at least great enough for said sensor means to calculate the reactant gas uptake attributable to the biological population.

4. The on-line respirometer of claim 1 wherein said sensor means comprises a dissolved oxygen probe inserted into said headspace.

5. The on-line respirometer of claim 1 wherein said sensor means comprises a dissolved oxygen probe inserted into slurry sample.

6. The on-line respirometer of claim 1 wherein said sensor means comprises a first dissolved oxygen probe inserted into said headspace and a second dissolved oxygen probe inserted into said slurry sample.

7. The on-line respirometer of claim 1 further comprising a pump operatively connected to said gas inlet to selectively introduce and recirculates said gas through the slurry sample.

8. The on-line respirometer of claim 1 wherein the inner chamber of said reaction vessel is constructed to prevent additional amounts of said gas and said slurry sample from entering said inner chamber.

9. The on-line respirometer of claim 1 wherein said gas inlet is adapted to introduce said gas directly into said slurry sample.

* * * * *